US008364240B2

(12) United States Patent
Krauss

(10) Patent No.: US 8,364,240 B2
(45) Date of Patent: Jan. 29, 2013

(54) METHOD AND DEVICE FOR AUTOMATICALLY DIFFERENTIATING TYPES OF KIDNEY STONES BY MEANS OF COMPUTED TOMOGRAPHY

(75) Inventor: Bernhard Krauss, Burgthann (DE)

(73) Assignee: Siemens Aktienegesellschaft, Munich (DE)

( * ) Notice: Subject to any disclaimer, the term of this patent is extended or adjusted under 35 U.S.C. 154(b) by 1041 days.

(21) Appl. No.: 11/730,274

(22) Filed: Mar. 30, 2007

(65) Prior Publication Data
US 2007/0249933 A1 Oct. 25, 2007

(30) Foreign Application Priority Data
Mar. 31, 2006 (DE) .......................... 10 2006 015 454

(51) Int. Cl.
*A61B 6/00* (2006.01)
(52) U.S. Cl. ............ 600/407; 600/425; 600/427; 378/5; 378/53; 378/62
(58) Field of Classification Search ............ 600/425, 600/427, 407; 378/4, 5, 9, 21, 37, 44, 45, 378/51, 53, 54, 62; 382/128, 131, 132
See application file for complete search history.

(56) References Cited

U.S. PATENT DOCUMENTS

| | | | | |
|---|---|---|---|---|
| 4,792,900 | A * | 12/1988 | Sones et al. | .................. 600/407 |
| 5,838,758 | A * | 11/1998 | Krug et al. | ...................... 378/53 |
| 6,597,759 | B2 * | 7/2003 | Mazess et al. | .................. 378/53 |
| 2005/0195936 | A1 * | 9/2005 | Raman et al. | ..................... 378/6 |

OTHER PUBLICATIONS

Chee Saw, K. et al., Helical CT of Urinary Calculi: Effect of Stone Composition, Stone Size, and Scan Collimation, AJR: 175, Aug. 2000, 329-332.*
Sheir, K., Determination of the chemical composition of uniary calculi by noncontrast spiral computerized tomography, Urol Res 33: 99-104 (Jan. 2005).*
Mohammad R. et al., Accurate Determination of chemical composition of urinary calculi by spiral computerized tomography. The Journal of Urology, vol. 159, 673-675, Mar. 1998, USA.

* cited by examiner

*Primary Examiner* — Brian Casler
*Assistant Examiner* — Rajeev Siripurapu
(74) *Attorney, Agent, or Firm* — Harness, Dickey & Pierce, P.L.C.

(57) ABSTRACT

At least one example embodiment relates to a method and/or a device for automatically differentiating types of kidney stones using computed tomography. The method provides two image data records of two computed tomography pictures of an object area including the kidney stones that have been recorded in the context of a different spectral distribution of the X-radiation. For each voxel of a slice of the object area that has X-ray attenuation values typical of kidney stones there is calculated from the two image data records a ratio r that is yielded from X-ray attenuation values of the voxel and prescribed X-ray attenuation values of pure urine in the context of the different spectral distributions of the X-radiation. The respective voxel is assigned to one of at least two types of kidney stones as a function of the variable r.

20 Claims, 2 Drawing Sheets

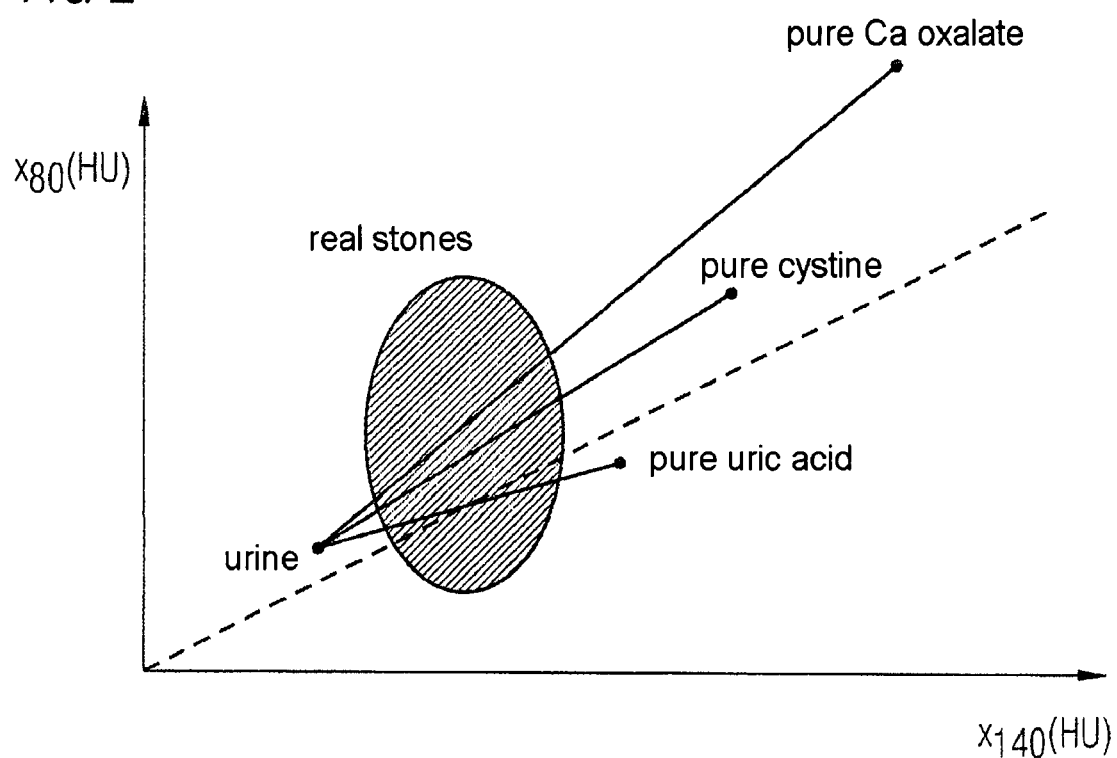

METHOD AND DEVICE FOR AUTOMATICALLY DIFFERENTIATING TYPES OF KIDNEY STONES BY MEANS OF COMPUTED TOMOGRAPHY

PRIORITY STATEMENT

The present application hereby claims priority under 35 U.S.C. §119 on German patent application numbers DE 10 2006 015 454.1 filed Mar, 31, 2006, the entire contents of each of which is hereby incorporated herein by reference.

FIELD

Embodiments of the present application generally relate to a method and/or a device for automatically differentiating types of kidney stones by way of computed tomography. For example, it may relate to one in which two computed tomography pictures of an object area including kidney stones are recorded in the context of a different spectral distribution of the X-radiation, and there are reconstructed from raw data of the two computed tomography pictures two image data records of the object area that include X-ray attenuation values of voxels of the object area in the context of the respective spectral distribution of the X-radiation.

BACKGROUND

Identifying and distinguishing different types of kidney stones in the human or animal body is very important in deciding on a therapy. Uric acid stones, cystine stones, oxalate stones or hydroxyapatite stones, for example count among the different types of kidney stones. It is chiefly the differentiation between uric acid stones and other types of kidney stones that is of great importance here, since the therapy of uric acid stones differs substantially from those of the other types.

Three different methods have been known to date for differentiating types of kidney stones. In the first method, the uric acid concentration in the blood is determined chemically. A high concentration indicates that a uric acid stone could be present. In the second method, solid constituents are filtered out of the urine. Thus, constituents of kidney stones can sometimes be detected in the urine after bodily movement, for example, through climbing steps, and be suitably investigated. In the third method, a surgical intervention is performed in which the kidney stone is already removed for the purpose of simultaneous diagnosis and therapy. It is possible to classify kidney stones with the aid of conventional computed tomography only with difficulty, since kidney stones do not occur as pure, compact substances. Although, for example, pure calcium oxalate is clearly distinguished from crystallized uric acid in the X-ray attenuation value, the X-ray attenuation values can nevertheless be very similar in reality.

SUMMARY

At least one embodiment of the present invention specifies a method and/or a device for differentiating types of kidney stones that enable automatic differentiation of at least two types of kidney stones without surgical intervention.

In at least one embodiment of the present method, two computed tomography pictures of an object area that includes the kidney stones to be differentiated are recorded in the context of a different spectral distribution of the X-radiation, and two image data records of the object area are reconstructed from the raw data of the two computed tomography pictures. The two image data records include the X-ray attenuation values of the voxels of the object area in the context of the respective spectral distribution of the X-radiation. X-ray attenuation values can be understood here both as the attenuation coefficients μ and as values derived therefrom, such as the CT value.

The two computed tomography pictures are recorded by using a multi-imaging computer tomograph, for example a so-called dual energy computer tomograph, with the aid of which it is possible simultaneously or at least virtually simultaneously to record two computed tomography pictures with a different spectral distribution of the X-radiation or different X-ray energy. Different techniques for generating two computed tomography pictures with a different spectral distribution of the X-radiation are fundamentally known to the specialist. It is possible to this end, for example, to make use of a number of X-ray sources with a different X-radiation, different detectors of different spectral sensitivity, different filters in front of the X-ray sources and/or X-ray detectors, or else of a combination of said techniques.

In at least one embodiment of the present method, a ratio r is calculated from the two image data records for each voxel of at least one interesting slice of the object area if the mean value from the two assigned X-ray attenuation values of the respective voxel lies above a prescribed threshold value ($X_{min}$) that is characteristic of kidney stones. The ratio r is yielded in the following way:

$$r = \frac{x_1 - o_1}{x_2 - o_2}.$$

In this equation, $x_1$ represents either the measured X-ray attenuation value of the voxel in the context of one of the two different X-ray energies, or an X-ray attenuation value averaged for this X-ray energy, which will be examined more closely later. In the same way, $x_2$ represents either the measured X-ray attenuation value of the voxel in the context of the other X-ray energy, or an appropriately averaged X-ray attenuation value. The two X-ray attenuation values $x_1$, $x_2$ can either be extracted directly from the two image data records, or be calculated therefrom. The values $o_1$ and $o_2$ that also occur represent the X-ray attenuation values of pure urine in the context of the two X-ray energies. These values are prescribed. They are either already known, or can be determined in advance.

The basis for the calculation of the ratio r is a 3-material decomposition in which the respective voxel is interpreted from a mixture of the base materials of urine, first type of kidney stone, in particular uric acid stone, and another type of kidney stone. A cystine stone, an oxalate stone or a hydroxyapatite stone, for example, comes into consideration as other type of kidney stone. It has been found on the basis of simulations that the ratio r for a stone of constant chemical composition depends only slightly on the object diameter.

In this case, high values of r characterize calcium-containing stones such as, for example, hydroxyapatite stones or oxalate stones. Medium values of r are measured for cystine stones (high sulfur content). Low values of r are yielded for the uric acid stone. In this way, different types of kidney stones can be distinguished, in particular, uric acid stones can be distinguished from other types of kidney stones, by appropriately prescribing threshold values or value ranges for r.

After r has been determined, the respective voxel is therefore assigned to one of at least two types of kidney stones as a function of the magnitude of r. These appropriately classified voxels can then be displayed with colored highlighting in a computed tomography image, for example. Also possible in this case is a differently colored display for different types of kidney stones, that is to say as a function of the magnitude of r. The viewer can immediately identify the location and the type of kidney stone in the CT images, in particular whether what is involved here is a uric acid stone or another type of kidney stone.

At least one embodiment of the present method and/or the associated device therefore enable types of kidney stones to be automatically differentiated by way of computed tomography, that is to say without surgical intervention. At least one embodiment of the method requires neither an analysis of eliminated stone material nor an analysis of blood values.

In an advantageous development of at least one embodiment of the method, the X-ray attenuation values $x_1$, $x_2$ of the respective voxel are obtained by averaging. In this case, a three-dimensional volume area with a prescribed extent around the relevant voxel, also denoted below as central voxel, is firstly formed. The three-dimensional volume area preferably constitutes a spherical volume, but can also exhibit another shape, for example, a cuboid. All the voxels whose X-ray attenuation values fulfill a prescribed criterion that is characteristic of kidney stones are selected inside this volume area. An average X-ray attenuation value of the selected voxels is then calculated separately for each image data record, the two averaged X-ray attenuation values yielded therefrom being used to form the ratio r. This step enables the selection of neighboring voxels of the central voxel that are highly likely to constitute kidney stone voxels, without leading to smearing with constant range.

In an example refinement of at least one embodiment of the method, the steps for determining the ratio r are not carried out for all the voxels, but only for a portion of these voxels that is determined in the following way. Here, the number of the selected voxels is determined in the three-dimensional volume area whose X-ray attenuation values fulfill the prescribed criterion. If this number lies above a prescribed threshold value for the number of the selected voxels, the two X-ray attenuation values or averaged X-ray attenuation values for the central voxel are used or determined, and the ratio r is calculated. If, however, the number of the selected voxels lies below the threshold value, no further kind of calculation is carried out for the central voxel. It is then assumed that this voxel does not constitute a site with a kidney stone in the object area investigated.

In one refinement of at least one embodiment of the present method, it is possible to use as criterion in accordance with which the voxels are selected inside the three-dimensional volume area the fact that the mean value of the two X-ray attenuation values of the respective voxel must lie above a threshold value that constitutes a lower limit for the presence of kidney stones.

However, it is preferred in the case of this criterion for the basis to be not the mean value, but a combined X-ray attenuation value that represents a weighted value $x_m$ dependent on the image noise ratio q between the two computed tomography pictures, and is calculated using the following rule:

$$x_m = \frac{x_1 - m \cdot x_2}{1 - m}, \text{ in which case } m = -\frac{q^2}{r_{ua,max}}.$$

The image noise ratio q is yielded from $q = dx_1/dx_2$, where $dx_1$ and $dx_2$ represent the statistical errors, that is to say the standard deviation, of the X-ray attenuation values $x_1$ and $x_2$.

The value $r_{ua,max}$ is a prescribed threshold value that specifies the upper threshold of the ratio r for uric acid.

This value is known or can be determined in advance. The voxels are then selected inside the three-dimensional volume area on the basis of the combined X-ray attenuation value $x_m$. All the voxels for which this combined X-ray attenuation value $x_m$ lies above a threshold value that represents a lower limit for the presence of kidney stones are selected. This mode of procedure based on the combined X-ray attenuation value that represents a weighted mean value dependent on the image noise ratio q substantially reduces the risk of an erroneous selection, caused by the image noise, in the vicinity of the threshold value of $x_m$, and so a more reliable result is attained. The ratio q of the image noise of the two image data records that is required for this purpose can already be known for the computed tomography installation being used, or be determined in advance from the two image data records, or else other image data records, for example topograms recorded in advance.

The device for automatically differentiating types of kidney stones by way of computed tomography pictures includes, in addition to a memory unit for the two image data records as main constituent, a determination module that carries out the calculations and determinations in accordance with the previously described method and, if appropriate, the individual developments of this method. The determination module is in this case preferably implemented in the image computer or a computed tomography installation that can supply the raw data for the two computed tomography pictures in the context of a different spectral distribution of the X-radiation. In this case, the device also includes an image reconstruction module that reconstructs the two image data records of the object area from the raw data of the two computed tomography pictures.

In one refinement, at least one embodiment of the device can, however, also include only the determination module with the memory unit, and an interface via which already reconstructed image data records from the two computed tomography pictures are received. The determination module is, for example, connected to an image display module that enables a colored image display of the voxels representing the kidney stones on an appropriate image display unit.

BRIEF DESCRIPTION OF THE DRAWINGS

The present method is explained once again briefly below with the aid of an example embodiment in conjunction with the drawings, in which:

FIG. 2 shows an illustration for the 3-material decomposition carried out in an embodiment of the method.

DETAILED DESCRIPTION OF THE EXAMPLE EMBODIMENTS

Figure 1:
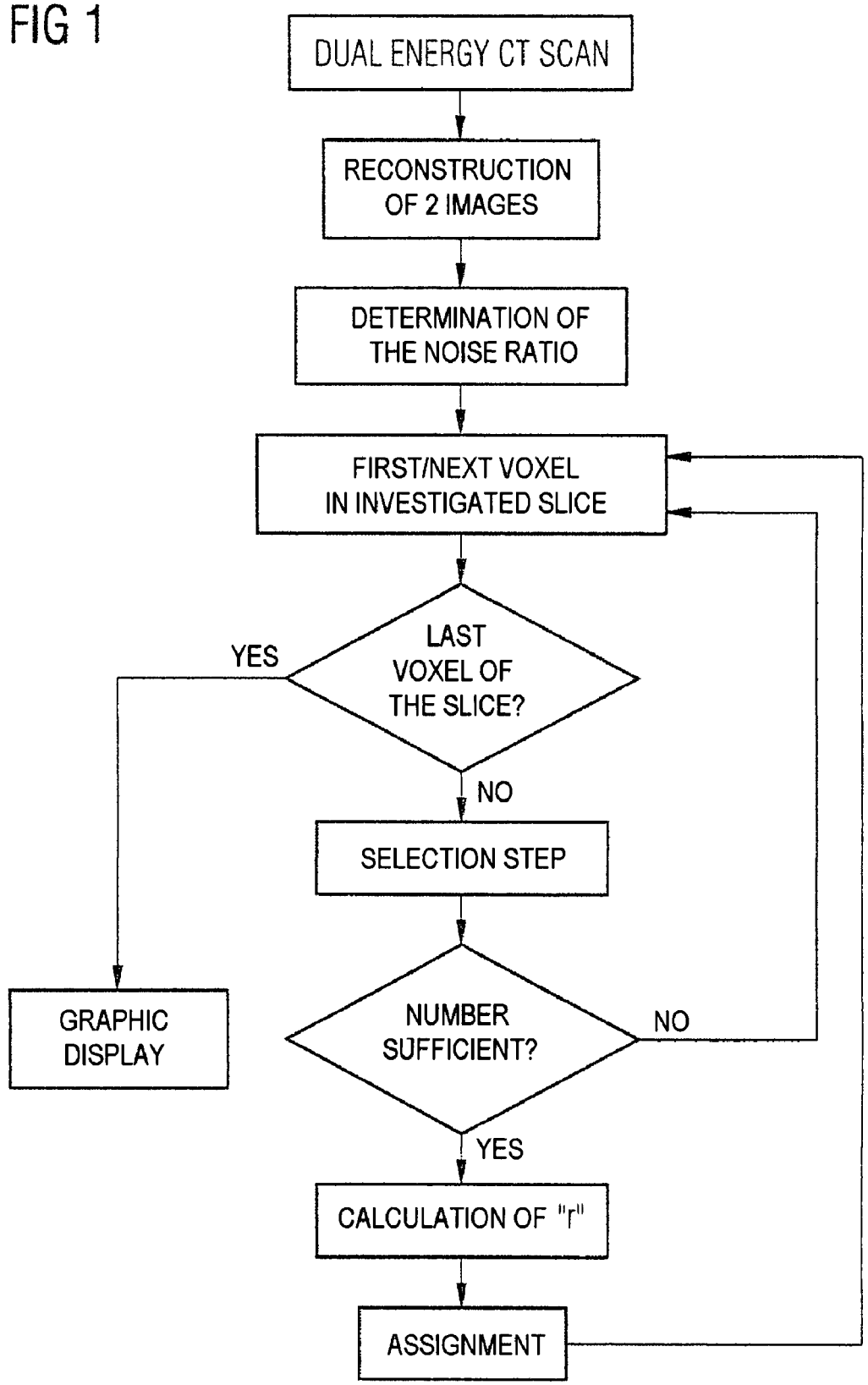
FIG. 1 shows an example of a method cycle in carrying out an embodiment of the present method.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

In the present example embodiment, a dual energy computer tomograph is used to carry out a dual energy CT scan of the object, in which raw data are simultaneously obtained in the context of two different X-ray energies. These different X-ray energies are obtained by means of a different tube voltage of the X-ray tubes used, 80 kV and 140 kV in the present example. Two CT images are reconstructed independently of one another from the raw data via known reconstruction algorithms. Each of the two image data records obtained in this case comprises for each voxel of the investigation volume a corresponding HU value for the respective X-ray energy.

Irrespective of the data recording and the computer tomograph used, it should be ensured in this case that the HU values for the body materials to be differentiated are to some extent stable when they occur or are positioned at different sites inside the object being investigated. This is, however, the case for most commercially available computer tomographs.

In the present example embodiment, only an axial slice is considered during preprocessing. If the ratio q of the image noise between the image for 80 kV and the image for 140 kV is not known for this slice, this ratio q can, for example, be determined approximately from the object diameter or the measured noise of the HU values of air. It is possible to this end, for example, to calculate for both tube voltages the mean noise for all the pixels of the slice below a certain threshold, for example, below −950 HU, in the upper half of the image, and to form the ratio subsequently. It is likewise possible to determine this ratio from a previously recorded topogram, for example.

In addition to the slice being investigated, a number of voxel slices above and below it are also required for the main portion of the processing. The term "combined HU value" used below denotes the weighted mean value $x_m$, dependent on the image noise ratio, of the HU values for 80 kV and 140 kV ($x_{80}$ and $x_{140}$, respectively). This can be calculated from the ratio q and the prescribed upper threshold value $r_{ua,max}$ used later, for uric acid:

$$x_m = \frac{x_{80} - m \cdot x_{140}}{1 - m}, \text{ in which case } m = -\frac{q^2}{r_{ua,max}}.$$

By contrast therewith the term "averaged HU value" is calculated as the arithmetic mean from the HU values for 80 kV and 140 kV, $x_{80}$ and $x_{140}$.

The following two steps are then carried out (cf. FIG. 1) for each voxel in the slice being investigated, given that the averaged HU value of this voxel lies above a typical threshold for kidney stones:

1. Selection step: a three-dimensional spherical environment of the investigated voxel is considered. Use is made only of voxels whose combined HU value lies above the threshold for kidney stones. In this way, all the neighboring voxels possibly having the same chemical composition are firstly selected. If the averaged HU value lies above the HU threshold for kidney stones for fewer than $n_{min}$ voxels in the volume considered, the following steps are omitted and no material assignment is made. Otherwise, a mean HU value $x8_0$ is calculated for this selected voxel for 80 kV, and a mean HU value $x_{140}$ is calculated for 140 kV, this being done in each case by averaging over the HU values of all the selected voxels. A radius of 7 voxels can be adopted as an example of the spherical environment, and a value of 100 voxels can be adopted as an example of the threshold value $n_{min}$. Of course, these values can, however, also be selected otherwise, depending on the application and image quality.

2. 3-material decomposition: the selected voxels are interpreted as a mixture of the base materials of urine (HU values: $o_{80}$ and $o_{-140}$), uric acid stone and cystine stone or oxalate/hydroxyapatite stone. The ratio $$r = \frac{x_{80} - o_{80}}{x_{140} - o_{140}}$$

is calculated.

High values of r characterize calcium-containing stones (hydroxyapatite stones, oxalate stones); medium values of r are measured for cystine stones (high sulfur content); low values of r are yielded for uric acid stones. It is very possible to distinguish uric acid stones and all other types of kidney stones on the basis of a clear difference in the value of r, since uric acid contains no relatively heavy atoms. Depending on image quality, however, an embodiment of the present method also enables other types of kidney stones to be distinguished. The material determined via the value r is now assigned to the central voxel. Once the image data record, or the interesting slice therein is completely processed, the material map thus prepared can be used to mark the types of kidney stones found in color in the CT image.

For illustrative purposes, FIG. 2 shows the X-ray attenuation values for urine, pure uric acid, pure cystine and pure calcium oxalate in a diagram where the X-ray attenuation values for 80 kV are plotted against the X-ray attenuation values for 140 kV. The X-ray attenuation values of real kidney stones lie in the hatched zone. The ratio r used in an embodiment of the present method corresponds to the gradient of the connecting line between the data point for pure urine and the data point that is yielded from the two measured (or averaged) X-ray attenuation values for a type of kidney stone. The types of kidney stones can be differentiated in an embodiment of the present method on the basis of the different gradients of the connecting lines for the different types of kidney stones.

The following parameters are required in this example to carry out an embodiment of the method:

| Parameter | Meaning |
| --- | --- |
| $x_{min}$ | Lower threshold (HU) for kidney stone voxels |
| $s_{take}$ | Radius of the volume considered |
| $n_{min}$ | Minimum number of voxels above the kidney stone threshold |
| $o_{80}$ | HU value of urine for 80 kV |
| $o_{140}$ | HU value of urine for 140 kV |
| $r_{ua,max}$ | Upper threshold of r for uric acid |

Even though the variable r was calculated in the present example on the basis of a spherical volume, it is, of course, also possible to calculate on the basis of other fundamentals. Thus, for example, r can be calculated for the voxels of a cuboid volume that contains the complete stone. Likewise, it is also possible to analyze only the central region of the stone, or even only single voxels.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatically differentiating types of kidney stones via computed tomography, the method comprising:

recording two computed tomography 3D-raw-data sets of an object area including kidney stones, each of the two computed tomography 3D-raw-data sets being associated with a different spectral distribution of an X-radiation;

reconstructing, from the two 3D-raw-data sets, two 3D-image data records of the object area that include at least two X-ray attenuation values of voxels of the object area;

determining if a mean value of the at least two X-ray attenuation values of voxels associated with one slice of the object area is above a threshold value that is characteristic of kidney stones; and if the determining step determines the mean value is above the threshold value, calculating from the two 3D-image data records, for each voxel of the at least one slice of the object are, a ratio r based on at least one of the at least two X-ray attenuation values of the voxels and from two averaged X-ray attenuation values that are obtained by averaging the at least two X-ray attenuation values of voxels inside a prescribed volume around the voxel in the respective 3D-image data record, and prescribed X-ray attenuation values $o_1$, $o_2$ of pure urine:

$$r = \frac{x_1 - o_1}{x_2 - o_2}$$

each of $x_1$ and $x_2$ being at least one of the at least two X-ray attenuation values and averaged X-ray attenuation values, the respective voxel being assigned to at least one type of kidney stones as a function of the magnitude of r, wherein for each voxel whose mean value from the at least two assigned X-ray attenuation values of the two 3D-image data records lies above the threshold value that is characteristic of kidney stones, firstly a three-dimensional volume area around the voxel is defined.

2. The method as claimed in claim 1, wherein the voxels of at least one type of kidney stone are displayed with colored highlighting in a CT image of the object area.

3. The method as claimed in claim 1, wherein, there are selected inside the volume area all the voxels whose X-ray attenuation values fulfill a criterion that is characteristic of kidney stones, and an averaged X-ray attenuation value of the selected voxels is calculated separately for each 3D-image data record in order to determine the ratio r from the two averaged X-ray attenuation values.

4. The method as claimed in claim 1, wherein, for each voxel whose mean value from the at least two assigned X-ray attenuation values of the two 3D-image data records lies above the prescribed threshold value that is characteristic of kidney stones, firstly a three-dimensional volume area with a prescribed extent around the voxel is defined, there are selected inside the volume area all the voxels whose X-ray attenuation values fulfill a prescribed criterion that is characteristic of kidney stones, a number of the selected voxels in the volume area is determined and is compared with a prescribed threshold value for the number, and an averaged X-ray attenuation value of the selected voxels is calculated separately for each image data record in order to determine the ratio r from the two averaged X-ray attenuation values, the calculation of the averaged X-ray attenuation values, and the determination of the ratio r of the averaged X-ray attenuation values being carried out only in the case of voxels where the number of selected voxels exceeds the prescribed threshold value for the number.

5. The method as claimed in claim 3, wherein the definition of the prescribed criterion is that the mean value of the at least two X-ray attenuation values of the voxel lies above the threshold value that is characteristic of kidney stones.

6. The method as claimed in claim 3, wherein the definition of the prescribed criterion is that a combined X-ray attenuation value $x_m$ of the voxel lies above the threshold value that is characteristic of kidney stones, the combined X-ray attenuation value being obtained from the following calculation rule:

$$x_m = \frac{x_1 - m \cdot x_2}{1 - m}, \text{ in which case } m = -\frac{q^2}{r_{ua,max}},$$

$x_1$ and $x_2$ representing the at least two X-ray attenuation values of the voxel, $r_{ua,max}$ representing an upper threshold value of the ratio r for uric acid, and q representing the ratio of the image noise of the images of the two image data records.

7. The method as claimed in claim 6, wherein the ratio q of the image noise is determined in a preprocessing step from the two image data records or topograms recorded in advance.

8. A device for automatically differentiating types of kidney stones via computed tomography, the device comprising:

a memory unit to store two 3D-image data records of an object area obtained from two computed tomography 3D-raw-data sets of the object area, each of the two computed tomography 3D-raw-data sets being associated with a different spectral distribution of the X-radiation, the two 3D-image data records including at least two X-ray attenuation values of voxels of the object area; and a determination module to, determine if a mean value of the at least two X-ray attenuation values of voxels associated with one slice of the object area is above a threshold value that is characteristic of kidney stones, if the determination module determines the mean value is above the threshold value, calculate from the two 3D-image data records, for each voxel of the at least one slice of the object area, a ratio r based on at least one of the at least two X-ray attenuation values of the voxels and from two averaged X-ray attenuation values obtained by averaging the at least two X-ray attenuation values of voxels inside a prescribed volume around the voxel in the respective 3D-image data record, and prescribed X-ray attenuation values $o_1, o_2$ of pure urine:

$$r = \frac{x_1 - o_1}{x_2 - o_2}$$

each of $x_1$ and $x_2$ being at least one of the at least two X-ray attenuation values and averaged X-ray attenuation values, the respective voxel of the at least two types of kidney stones being assigned as a function of the magnitude of r, and for each voxel whose mean value from the at least two assigned X-ray attenuation values of the two image data records lies above the prescribed threshold value that is characteristic of kidney stones, firstly define a three-dimensional volume area with a prescribed extent around the voxel.

9. The device as claimed in claim 8, wherein the determination module is further configured to select inside the volume area all the voxels whose at least two X-ray attenuation values fulfill a prescribed criterion that is characteristic of kidney stones, and to calculate an averaged X-ray attenuation value of the selected voxels separately for each image data record in order to determine the ratio r from the at least two averaged X-ray attenuation values.

10. The device as claimed in claim 8, wherein the determination module is further designed to, for each voxel whose mean value from the at least two assigned X-ray attenuation values of the two image data records lies above the prescribed threshold value that is characteristic of kidney stones, firstly define a three-dimensional volume area with a prescribed extent around the voxel, to select inside the volume area all the voxels whose X-ray attenuation values fulfill a prescribed criterion that is characteristic of kidney stones, to determine a number of the selected voxels in the volume area and to compare them with a prescribed threshold value for the number, and to calculate an averaged X-ray attenuation value of the selected voxels separately for each image data record in order to determine the ratio r from the two averaged X-ray attenuation values, the calculation of the averaged X-ray attenuation values and the determination of the ratio r of the averaged X-ray attenuation values being carried out only in the case of voxels where the number of selected voxels exceeds the prescribed threshold value for the number.

11. The device as claimed in claim 9, wherein the definition of the prescribed criterion is that the mean value of the at least two X-ray attenuation values of the voxel lies above the threshold value that is characteristic of kidney stones.

12. The device as claimed in claim 9, wherein the definition of the prescribed criterion is that a combined X-ray attenuation value $x_m$ of the voxel lies above the threshold value that is characteristic of kidney stones, the combined X-ray attenuation value being obtained from the following calculation rule:

$$x_m = \frac{x_1 - m \cdot x_2}{1 - m}, \text{ in which case } m = -\frac{q^2}{r_{ua,max}},$$

$x_1$ and $x_2$ representing the at least two X-ray attenuation values of the voxel, $r_{ua,max}$ representing an upper threshold value of the ratio r for uric acid, and q representing the ratio of the image noise of the images of the two image data records.

13. The method as claimed in claim 2, wherein, for each voxel whose mean value from the at least two assigned X-ray attenuation values of the two image data records lies above the prescribed threshold value that is characteristic of kidney stones, firstly a three-dimensional volume area with a prescribed extent around the voxel is defined, there are selected inside the volume area all the voxels whose X-ray attenuation values fulfill a prescribed criterion that is characteristic of kidney stones, and an averaged X-ray attenuation value of the selected voxels is calculated separately for each image data record in order to determine the ratio r from the two averaged X-ray attenuation values.

14. The method as claimed in claim 2, wherein, for each voxel whose mean value from the at least two assigned X-ray attenuation values of the two image data records lies above the prescribed threshold value that is characteristic of kidney stones, firstly a three-dimensional volume area with a prescribed extent around the voxel is defined, there are selected inside the volume area all the voxels whose X-ray attenuation values fulfill a prescribed criterion that is characteristic of kidney stones, a number of the selected voxels in the volume area is determined and is compared with a prescribed threshold value for the number, and an averaged X-ray attenuation value of the selected voxels is calculated separately for each image data record in order to determine the ratio r from the two averaged X-ray attenuation values, the calculation of the averaged X-ray attenuation values, and the determination of the ratio r of the averaged X-ray attenuation values being carried out only in the case of voxels where the number of selected voxels exceeds the prescribed threshold value for the number.

15. The method as claimed in claim 4, wherein the definition of the prescribed criterion is that the mean value of the at least two X-ray attenuation values of the voxel lies above the threshold value that is characteristic of kidney stones.

16. The method as claimed in claim 4, wherein the definition of the prescribed criterion is that a combined X-ray attenuation value $x_m$ of the voxel lies above the threshold value that is characteristic of kidney stones, the combined X-ray attenuation value being obtained from the following calculation rule:

$$x_m = \frac{x_1 - m \cdot x_2}{1 - m}, \text{ in which case } m = -\frac{q^2}{r_{ua,max}},$$

$x_1$ and $x_2$ representing the two X-ray attenuation values of the voxel, $r_{ua,\,max}$ representing an upper threshold value of the ratio r for uric acid, and q representing the ratio of the image noise of the images of the two image data records.

17. The device as claimed in claim 10, wherein the definition of the prescribed criterion is that the mean value of the at least two X-ray attenuation values of the voxel lies above the threshold value that is characteristic of kidney stones.

18. The device as claimed in claim 10, wherein the definition of the prescribed criterion is that a combined X-ray attenuation value $x_m$ of the voxel lies above the threshold value that is characteristic of kidney stones, the combined X-ray attenuation value being obtained from the following calculation rule:

$$x_m = \frac{x_1 - m \cdot x_2}{1 - m}, \text{ in which case } m = -\frac{q^2}{r_{ua,max}},$$

$x_1$ and $x_2$ representing the at least two X-ray attenuation values of the voxel, $r_{ua,max}$ representing an upper threshold value of the ratio r for uric acid, and q representing the ratio of the image noise of the images of the two image data records.

19. A device for automatically differentiating types of kidney stones via computed tomography, the device comprising:
means for storing two 3D-image data records of the object area obtained from two computed tomography 3D-raw-data sets of the object area, each of the two computed tomography 3D-raw-data sets being associated with a different spectral distribution of the X-radiation, the two 3D-image data records including at least two X-ray attenuation values of voxels of the object area; and
means for determining if a mean value of the at least two X-ray attenuation values of voxels associated with one slice of the object area is above a threshold value that is characteristic of kidney stones; and
if the means for determining determines the mean value is above the threshold value, means for calculating from the two 3D-image data records, for each voxel of the at least one slice of the object area, a ratio r based on at least one of the at least two X-ray attenuation values of the voxels and from two averaged X-ray attenuation values obtained by averaging the at least two X-ray attenuation values of voxels inside a prescribed volume around the voxel in the respective 3D-image data record, and prescribed X-ray attenuation values $o_1$, $o_2$ of pure urine:

$$r = \frac{x_1 - o_1}{x_2 - o_2}$$

each of $x_1$ and $x_2$ being at least one of the X-ray attenuation values and averaged X-ray attenuation, the respective voxel of the at least two types of kidney stones being assigned as a function of the magnitude of r, and
for each voxel whose mean value from the at least two assigned X-ray attenuation values of the two image data records lies above the prescribed threshold value that is characteristic of kidney stones, firstly define a three-dimensional volume area with a prescribed extent around the voxel.

20. The device as claimed in claim 19, wherein the means for calculating is further for, selecting inside the volume area all the voxels whose X-ray attenuation values fulfill a prescribed criterion that is characteristic of kidney stones, and for calculating an averaged X-ray attenuation value of the selected voxels separately for each image data record in order to determine the ratio r from the two averaged X-ray attenuation values.

* * * * *